United States Patent [19]

Herrmann et al.

[11] Patent Number: 5,342,985
[45] Date of Patent: Aug. 30, 1994

[54] ORGANIC DERIVATIVES OF RHENIUM OXIDES AND THEIR PREPARATION AND USE FOR THE METATHESIS OF OLEFINS

[75] Inventors: Wolfgang A. Herrmann, Freising; Werner Wagner, Munich; Ursula Volkhardt, Freising, all of Fed. Rep. of Germany

[73] Assignee: Hoechst AG, Frankfurt am Main, Fed. Rep. of Germany

[21] Appl. No.: 569,614

[22] Filed: Aug. 20, 1990

Related U.S. Application Data

[63] Continuation-in-part of Ser. No. 320,404, Mar. 8, 1989, abandoned.

[30] Foreign Application Priority Data

Dec. 10, 1988 [DE] Fed. Rep. of Germany ....... 3841733
Jan. 31, 1989 [DE] Fed. Rep. of Germany ....... 3902787
Mar. 28, 1990 [DE] Fed. Rep. of Germany ....... 4009910

[51] Int. Cl.$^5$ .............................. C07F 7/08; C07F 7/18
[52] U.S. Cl. ...................................... 556/482; 556/485; 560/130; 560/219; 560/205; 560/221; 568/626; 568/627; 568/630; 568/655; 568/685; 568/687; 570/135; 570/136; 585/510; 585/520

[58] Field of Search .............. 556/482, 485; 560/130, 560/219, 221, 205; 568/626, 627, 630, 655, 685, 687; 570/135, 136; 585/510, 520

*Primary Examiner*—Paul F. Shaver
*Attorney, Agent, or Firm*—Connolly & Hutz

[57] ABSTRACT

The invention relates to a process for the metathesis of olefins which comprises reacting an olefin of the formula $YCZ=CZ-(CX_2)_nR^2$ (II) wherein n is an integer from 1 to 28, X represents H or F, Y represents H or alkyl having from 1 to 10 carbon atoms and Z represents H or a non-aromatic hydrocarbon group having from 1 to 6 carbon atoms and $R^2$ represents H, alkyl, halogen, $COOR^3$ or $OR^4$, wherein $R^3$ and $R^4$ represent alkyl having from 1 to 15 carbon atoms or phenyl which is unsubstituted or contains from 1 to 3 substituents or wherein $R^4$ is trialkylsilyl $R^5Si$, wherein $R^5$ represents alkyl having from 1 to 5 carbon atoms, at a catalyst comprising an oxidic carrier charged with a rhenium compound as defined hereinbefore.

17 Claims, 8 Drawing Sheets

ORGANIC DERIVATIVES OF RHENIUM OXIDES AND THEIR PREPARATION AND USE FOR THE METATHESIS OF OLEFINS

This application is a continuation-in-part of our earlier application Ser. No. 320,404 filed Mar. 8, 1989, now abandoned.

The present invention relates to organic derivatives of rhenium oxides and to their preparation and use for the metathesis of olefins as such and also derivatives of olefins.

The term metathesis designates, as is known, the cleavage of olefinic compounds in such a way that the double bond is broken apart and the two fragments combine to form new compounds. In the wider sense, metathesis also includes the ring-opening polymerization of cycloolefins. In the specific case, where the said cleavage is carried out in the presence of the basic olefin ethylene, the reaction is a so-called ethenolytic metathesis also called ethenolysis. In this reaction the double bonds of the ethylene and of the other olefin are broken apart and the resulting fragments combine in a statistical manner to form new compounds. Where a symmetric mono-olefin is subjected to a ethenolysis, only a single product is formed, while two different products are formed if an unsymmetric mono-olefin is subjected to ethenolysis; when using di- or oligo-olefins, the number of the final products is increased accordingly. Again, in a wider sense ethenolysis of olefins also includes the ring-opening of cyclo-olefins, in which case an $\omega,\omega'$-diolefin having $n+2$ chain links is formed from a cyclo-olefin having n chain links.

As a result of the invention, an organorhenium compound of definite structure, which can be isolated in an undiluted form, becomes a catalyst for the first time.

Ethenolytic cleavages of olefins are of commercial interest for the preparation of fine chemicals and bulk chemicals. Examples of the catalytic ethenolysis in industry are the Phillips process for the preparation of 3,3-dimethyl-1-butene and the Shell process for the preparation of $\omega, \omega'$-diolefins which compounds are of industrial importance as crosslinking agents in the polymerisation of olefins or for the preparation of bifunctional compounds.

While it is the intention in the conventional metathesis of olefins, often called self-metathesis, to convert an unsymmetric olefin in two other olefins having a shorter or longer chain of carbon atoms, or to polymerise a cyclic olefin under ring-opening to yield a di- or higher polymerised product, the ethenolysis is distinguished from such self-metathesis by the fact that always α-olefins are produced in which the fragments which are formed by the splitting of the double bond of the starting olefin are always prolonged by one $CH_2$-group. Thus, the ethenolysis of olefins having non-terminal double bonds is the counter part of the self-metathesis of α-olefins.

The ethenolysis is in fact always to be carried out under elevated pressure and insofar it is somewhat distinguished from the conventional metathesis of olefins by its process conditions. Very often different catalysts are used for both kinds of metathesis.

It is known that compounds of the element rhenium exhibit catalytic activity in the metathesis of olefins, specifically only in the metathesis of olefins as such. Only if so-called co-catalysts, in particular tetraalkyltin compounds are added to such rhenium catalysts is the metathesis of derivatives of olefins, i.e. olefins containing heterofunctions, possible (K. J. Ivin: Olefin Metathesis, Academic Press, London 1983, 32-34). Thus the metathesis of olefinically unsaturated carboxylic acid esters and of allyl halides and the like on multi-component catalysts, such as $WCL_6/Sn(CH_3)_4$ or $Re_2O_7/Sn(CH_3)_4/Al_2O_3$ has been described. The last-named system (R. A. Fridman et al., Dokl. Akad. Nauk. SSSR 234, (1977), 1354-57; R. H. A. Bosma et al., J. Organometal. Chem. 225 (1983) 159-171; X. Xiaoding et al., J. Chem. Soc. Chem. Commun. 1985, 631-633; G. C. N. van den Aardweg, loc. cit. 1983, 262-263) is the only one containing rhenium which is capable of metathesizing olefinically unsaturated organic halides, esters and the like. Hitherto there has been no knowledge of the effective catalyst species. The following are practical disadvantages of the rhenium-containing catalyst systems hitherto used:

a) the necessity of using at the same time highly toxic tetraalkyltin compounds as activators in the metathesis of derivatives of olefins (J. E. Cremer, Biochem. J. 68 (1958) 685-688; W. N. Aldridge et al., The Lancet, Sep. 26, 1981, page 692/3), b) low catalyst activity, inacceptable for industrial use, and c) a breadth of application with relatively narrow limits, i.e. the catalytic action is only found in the case of simple derivatives of olefins or olefins as such.

It was therefore required to find a non-toxic and effective catalyst system which is as readily accessible, simple to handle and stable on storage as possible and which is also adequate without any activator in the metathesis of olefin derivatives. Considerable interest attaches to the industrial further processing of the products.

Although some so-called "organorhenium oxides", for example $CH_3ReO_3$, $(\eta^5-C_5(CH_3)_5)ReO_3$ (=pentamethylcyclopentadienylrhenium trioxide), are known as catalyst components for the metathesis of olefins by homogeneous catalysis W. A. Herrmann et al., Angew. Chem. 100 (1988) 420-422, translation in Angew. Chem. Int. Ed. Engl. 27 (1988) 394-396), the concomitant use, as activator, of a Lewis acid which is at least partially soluble in organic solvents was, however, always necessary, preferably aluminum(III) chloride and, in most cases, also the concomitant use of toxic tin tetraalkyls (for example $Sn(CH_3)_4$) as further activators. Even then the catalyst systems thus obtainable are completely inactive in respect of the metathesis of derivatives of olefins.

It has now been found, surprisingly, that methylrhenium trioxide $CH_3ReO_3$ and related compounds of the formula I indicated below are suitable for use as a metathesis catalyst when supported on oxide supporting materials, in particular aluminum oxide supports. The use of additional activator substances ("co-catalysts"), which is disadvantageous for many reasons, thus becomes superfluous for the first time.

The invention thus relates to the use of compounds of rhenium which have the general formula $R^1_aRe_bO_c$ (I) in which a is 1 to 6, b is 1 to 4 and c is 1 to 14 and the total of a, b and c is such that it accords with the pentavalency to heptavalency of rhenium, subject to the proviso that not greater than $3 \times b$, and which are supported on oxide supporting materials, as heterogeneous catalysts for metathesis. In this connection $R^1$ denotes an organic group attached to the metal rhenium via a carbon atom to which at least one hydrogen atom is still attached, specifically alkyl radicals having to 9 carbon atoms, cycloalkyl having 5 to 10 carbon atoms, such as cyclohexyl or 1-norbornyl, or aralkyl having 7 to 9 carbon atoms, such as benzyl, but preferably methyl. The terms alkyl and cycloalkyl naturally imply that these groups contain no multiple bonds. $R^1$ can be at least partially fluorinated, For steric reasons, however, the presence of more than three groups containing more than 6 carbon atoms per rhenium atom is not possible in the compounds; the compounds preferably contain only one such group at the most. The term metathesis in this context includes the ring-opening polymerization of cycloolefins and the ethenolysis.

Of the compounds of the formula mentioned above, $CH_3ReO_3$, $(CH_3)_6Re_2O_3$ and pentamethylcyclopentadienylrhenium trioxide are admittedly known, but the catalytic activity of these compounds without the concomitant use of activators, that is to say their suitability as the sole catalyst, was not known and was as unexpected as that of the whole class of compounds. This catalytic action is all the more surprising because (trimethylstannoxy)-rhenium trioxide [$(CH_3)_3SnO$]-$ReO_3$, which is isostructural, is catalytically inactive. This shows the importance of the alkyl groups attached to rhenium for the catalytic activity of the compounds according to the invention.

The invention therefore also relates to the compounds of the abovementioned formula I, with the exception of $CH_3ReO_3$, $(CH_3)_6Re_2)O_3$ and pentamethylcyclopentadienylrhenium trioxide.

Figure 1:
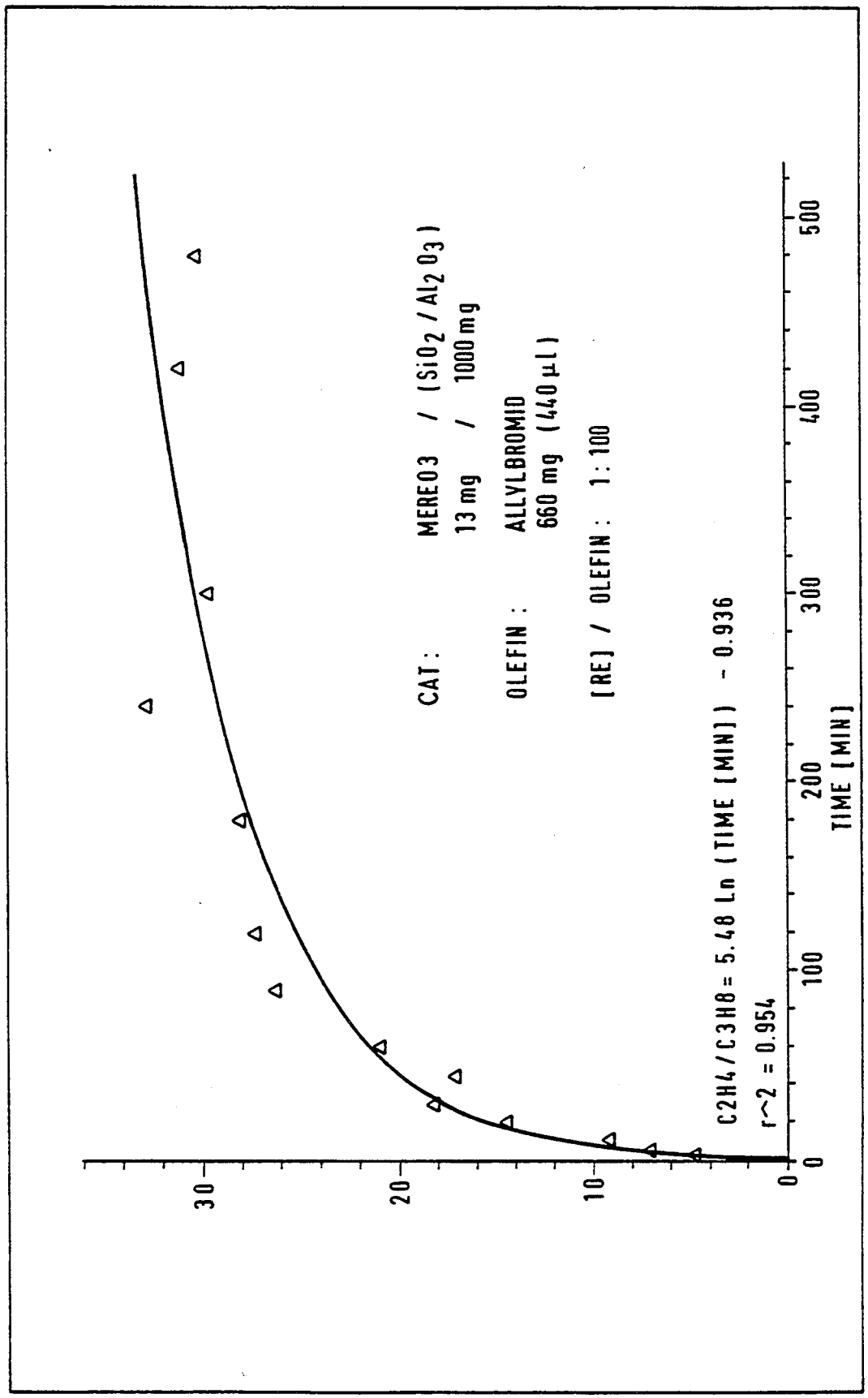
FIGS. 1 through 8 are graphical plots illustrating product distributions when olefins are subject to metathesis in accordance with the claimed invention and in processes using known catalyst systems.

In terms of synthesis, the compounds according to the invention can be synthesized in a very simple manner from $Re_2O_7$ by means of customary alkylating agents. For example, dirhenium heptoxide is reacted in an anhydrous solvent which is inert towards the rhenium compounds, at a temperature from 0° to 60°, preferably 10° to 40° C., with a solution of $R^1{}_2Zn$ in which $R^1$ has the meaning indicated above, and the volatile constituents are removed. The compounds according to the invention are entirely insensitive to air and moisture. When supported on oxidic supporting materials, the rhenium compounds are highly active catalysts for the metathesis of olefins as such—including the ethenolysis—and also of derivatives of olefins of the type $YCZ=CZ-(CX_2)_nR^2$ (II) in which n is an integer from 1 to 28, X is H or F, Y is H or alkyl having 1 to 10 carbon atoms and Z represents H or a non-aromatic hydrocarbon radical having 1 to 6 carbon atoms, for example cyclohexyl, but preferably open-chain alkyl having 1 to 4 carbon atoms, and the substituent $R^2$ is alkyl, halogen, $COOR^3$ or $OR^4$ in which $R^3$ is alkyl or aryl and $R^4$ is alkyl, aryl or trialkylsilyl $R^5{}_3Si$. Compounds, in which $R^2$ is halogen, $COOR^3$ or $OR^4$ in which $R^3$ and $R^4$ have the aforementioned meaning, are also designated as functionalized olefins. The alkyl groups in $R^5$ contain 1 to 5, preferably 1 to 3 carbon atoms. In $R^3$ and $R^4$ alkyl represents 1 to 15, preferably 1 to 6, carbon atoms and aryl represents phenyl which can also contain one to three substituents on the ring, such as halogen, for example fluorine, chlorine or bromine, $NO_2$, $NR^6R^7$, $OR^8$and/or alkyl. The radicals $R^6$, $R^7$ and $R^8$ are identical or different and can be hydrogen or alkyl having 1 to 4 carbon atoms. However, the groups YCZ and $CZ-(CH_2)_nR^2$ must be different except when used as a reactant in the ethenolysis. In the ethenolysis, however, Y and Z preferably do not simultaneously mean halogen.

If $R^2$ in formula II is halogen, it can be fluorine, chlorine, bromine or iodine. Both Z may be equal or different. If Z is hydrogen and $R^2$ is halogen, the latter is preferably bromine. Examples of compounds in which at least one X is F are 4-(perfluoro-n-hexyl)but-1-ene, formula $(n-C_6F_{13})-CH_2-CH_2-CH=CH_2$, 1,6-di-(perfluoro-n-hexyl)-hexene(3) of the formula $(n-C_6F_{13})-CH_2-CH_2-CH=CH-CH_2-CH_2-(n-C_6F_{13})$ and perfluoropropene $C_3F_6$. The number n of units varies, preferably within the range from 1 to 12 and especially up to 8. Suitable cyclic hydrocarbons and other cycloolefinic compounds having one or more olefinic bonds are for example cyclooctene, 1,5-cyclooctadiene and cycloolefins having up to 20 carbon atoms, and cyclic di- and oligo-olefinic compounds which contain functional groups with hetero atoms.

The novel catalysts are thus not only active in the case of olefins in which Z=H, but also, for the first time, in the metathesis of partly or completely fluorinated olefins. They are also suitable for the metathesis of non-terminal olefin derivatives of the formula $R^9CH=CH-(CH_2)_nR^{10}$ (IV) in which $R^9$ is a branched, or preferably unbranched, alkyl radical having 1 to 12 carbon atoms, $R^{10}$ is a carboxyalkyl radical in which the alkyl radical preferably has 1 to 4 carbon atoms, and n represents an integer from 1 to 10. Methyl oleate ($R^9$=n-octyl, $R^{10}$=$CO_2CH_3$ and n=7) may be mentioned as an example. They are also, and this being surprising, suitable for the ethenolysis of olefins, i.e. splitting acyclic and cyclic olefins whether they have functional groups or not, in the presence of ethylene. This is the more surprising, as the (trimethylstannoxy)rhenium trioxide which is of an analogous structure, shows no catalytic activity in the ethenolysis, and neither other oxidic rhenium compounds, such as dirhenium heptoxide $Re_2O_7$, various perrhenates with the anion $[ReO_4]^-$, the rhenium trioxide $ReO_3$ and the other rhenium oxides $Re_2O_5$ and $ReO_2$.

$SiO_2/Al_2O_3$ (for example in a ratio by weight of 87:13) and $Al_2O_3$, each of which can be acid, neutral or basic according to its pretreatment, are particularly suitable as supporting materials. The activity of these catalysts can be increased considerably if the rhenium compounds are supported on a thoroughly calcined, i.e. as far as possible anhydrous, support, such as silica/aluminum oxide. This is because if the supporting material contains major amounts of moisture, the activity decreases, because the alkyl group attached to rhenium is then partly split off as alkane by means of the water. Other suitable oxidic supporting materials are oxides of titanium, zirconium, niobium, tantalum and chromium alone or in combination with each other, particularly with alumina, silica or both.

The catalytic activity of the catalysts according to the invention for the metathesis of olefins is higher than that of the rhenium-containing catalyst systems described hitherto. An exemplary proof is afforded by the systems A1 and V1 (cf. the graphs set forth in FIGS. 1 and 6). The system $CH_3ReO_3/SiO_2/Al_2O_3$ (see FIG. 1) metathesizes allyl bromide in only 20 minutes to a Q of over 20, the ratio $Q = \frac{\text{peak area of ethylene}}{\text{peak area of propane}}$ being obtained using propane as predetermined standard and being plotted against time. The shape of the curve provides information on the activity of the particular catalyst systems. The standard catalyst $NH_4[ReO_4]/SiO_2/Al_2/O_3$ (see FIG. 6) known from the literature is, in contrast, only active in the presence of $Sn(CH_3)_4$, and even then only to a comparable extent in 180 minutes. The symbol "r∧2" is a measure of the agreement between the shape of the curve determined by calculation and the experimental values.

The rhenium-containing catalysts hitherto used industrially in olefin metathesis are, as a rule, prepared (see Warwel et al., Chem.-Ztg 107 (1983), 115–120) by treating commercially available ammonium perrhenate $NH_4[ReO_4]$ as a solution in dioxane/water with the supporting material (as a rule aluminum oxide). The resulting suspension is then evaporated to complete dryness in a water pump vacuum; the dry material is then heated at 550° C., first for about 2 hours in a stream of oxygen and then for about 2 hours in a stream of nitrogen. Only the material obtained in this way and cooled to room temperature is employed for catalytic purposes.

For the process according to the invention, on the other hand, it is possible to dispense with these time-consuming and energy-consuming process stages, as a result of which catalysts of better reproducibility are also obtained. For the present process, the catalytically active rhenium compound is applied, preferably at room temperature, from a solvent, preferably a solution of methylene dichloride, to the catalyst support, preferably silica gel/aluminum oxide, and only the catalyst support is freed from moisture, before use, for 2 hours at 550° C. to 800° C. in a stream of nitrogen, in order that the catalyst system may subsequently develop its full activity.

In metathesis using the catalysts according to the invention care must be taken that air and moisture are excluded. The olefins employed must also preferably be dried thoroughly before use. In general, the metathesis is carried out at atmospheric pressure and a temperature from 0° to 400° C., preferably 10° to 35° C. The fact that it is possible to work under such mild reaction conditions is a particular advantage of the process according to the invention. It is also possible, however, to use higher temperatures, for example up to 100° C., or to work under a pressure above or below atmospheric. Usually, however, no advantages are associated therewith.

The ethenolysis is carried out in general at a pressure of to 30, preferably 5 to 20 bar of ethylene and at a temperature in the range of −25° to +70° C., preferably of from +20° to +65° C. Higher temperatures, e.g. up to 100° C. may also be applied or in certain cases a lower pressure, e.g. atmospheric pressure. However, usually no advantages are achieved by such variations. It is a special advantage of the invention that it is possible to carry out the ethenolysis at so mild reaction conditions.

In the characterization of individual compounds in the following examples "sst" means very strong, "st" means strong, "br" means broad and "EI-MS" means electron impact mass spectrum.

EXAMPLES 1–5

Metathesis Using $CH_3ReO_3$

In the following tests the olefins employed were dried over $CaH_2$ and distilled before being used. The catalyst used in these tests was methylrhenium trioxide $CH_3ReO_3$ which had been prepared by a simple process in terms of preparation, avoiding toxic tetramethyltin, $Sn(CH_3)_4$, as follows:

20 ml of a 0.5-molar solution of dimethylzinc $Zn(CH_3)_2$ in tetrahydrofuran were added dropwise at room temperature and in the course of 10 minutes to a solution of 4.84 g (10 mmol) of dirhenium heptoxide $Re_2O_7$ (made by Degussa, 76.9% of Re) in 100 ml of an anhydrous solvent, such as tetrahydrofuran, and the mixture was then stirred for a further 60 minutes at room temperature. The volatile constituents were then stripped off under an oil pump vacuum into a cold trap. The residue was sublimed in a high vacuum at 40°–55° C. onto a water-cooled sublimation finger. This gave 3.89 g (78% of theory) of colorless, mostly needle-shaped, crystals of the catalyst $CH_3ReO_3$. The synthesis is also possible using unsublimed $Re_2O_7$, but the yields are then lower. The substance has the following characteristics: Melting point 106°. IR(cm−, KBr): 1002 sst, 950 sst,br [v(Re=O)].-$^1$H-NMR (CDCl$_3$, 28° C.): δ (CH$_3$)=2.61 [singlet]. $^{13}$C-NMR (CDCl$_3$, 28° C.): δ (CH$_3$)=19.03 [quartet, $^1$J(C,H)=138 Hz]. $^{17}$O-NMR (CDCl$_3$, 28° C: (O)=829 ppm. EI-MS: m/z=250 (molecule-ion, with the correct pattern of isotopes $^{185}$Re/$^{187}$Re). The substance can be stored at room temperature without decomposition. Elementary analysis: Calculated for $CH_3O_3Re$ (249.21): C 4.82, H 1.20, O 19.26, Re 74.72; found: C 4.84, H 1.19, O 19.30, Re 74.78.

In a 30 ml reaction vessel equipped with a septum, a reflux condenser and a mercury pressure relief valve, solution of 13 mg (0.052 mmol) of methylrhenium trioxide $CH_3ReO_3$ in 0.5 ml of methylene dichloride was introduced with stirring into a suspension of 1,000 mg of catalyst support [$SiO_2/Al_2O_3$ (87:13 by weight), particle size below 15 μm (preparation No. 14-7150 of Strem Chemicals, Newburyport/Mass. 01950 (USA), heated at 800° C. for 2 hours] in 10 ml of methylene dichloride (dried over calcium hydride and stored under an atmosphere of nitrogen). The contents of the flask were heated to the boil. After thermal equilibrium had been set up, 5.2 mmol of olefin were injected by means of a syringe through the septum. In order to isolate the product, the mixture was boiled for several hours under reflux (Table 1), the contact catalyst was filtered off with suction on a frit and was extracted by washing with twice 10 ml of methylene dichloride. The solvent was stripped off under an oil pump vacuum, the product was weighed and its purity was checked by means of a gas chromatograph with coupled mass spectrometer.

TABLE 1

Metathesis of α-olefin derivatives of the type II with the elimination of ethylene

| Example/olefin (*) | Time (hrs) | Amount (mg) | Weight (mg) | Purity (%) | Yield (%) |
|---|---|---|---|---|---|
| 1) Allyl bromide | 4 | 620 | 100 | 100 | 14 |
| 2) Ethyl undecenoate | 20 | 1120 | 1120 | 64 | 64 |
| 3) Allyl isopropyl ether | 4 | 520 | 220 | 70 | 30 |
| 4) Allyl ethyl ether | 5 | 448 | 260 | 50 | 39 |
| 5) Allyl trimethyl- | 24 | 680 | 530 | 88 | 69 |

TABLE 1-continued

Metathesis of α-olefin derivatives of the type II with the elimination of ethylene

| Example/olefin (*) | Time (hrs) | Amount (mg) | Weight (mg) | Purity (%) | Yield (%) |
|---|---|---|---|---|---|
| silyl ether | | | | | |

(*) Metathesis products:
1) 1,4-Dibromobut-2-ene.
2) Diethyl eicos-10-ene-ω,ω'-dicarboxylate.
3) 1,4-Bis-(isopropoxy)-but-2-ene.
4) 1,4-Bis-(ethoxy)-but-2-ene.
5) 1,4-Bis-(trimethylsiloxy)-but-2-ene.

Comparisons

In a 30 ml reaction vessel closed with a septum, a solution of 13 mg (0.052 mmol) of methylrhenium trioxide $CH_3ReO_3$ in 0.5 ml of methylene dichloride was introduced with stirring into a suspension of 1,000 mg of catalyst support ($SiO_2/Al_2O_3$ (weight ratio 87:13, particle size below 15 μm; kept at 800° C. for 2 hours)) in 10 ml of methylene dichloride (dried over calcium hydride and stored under an atmosphere of nitrogen). 0.5 ml of propane was injected as the internal standard.

Figure 2:
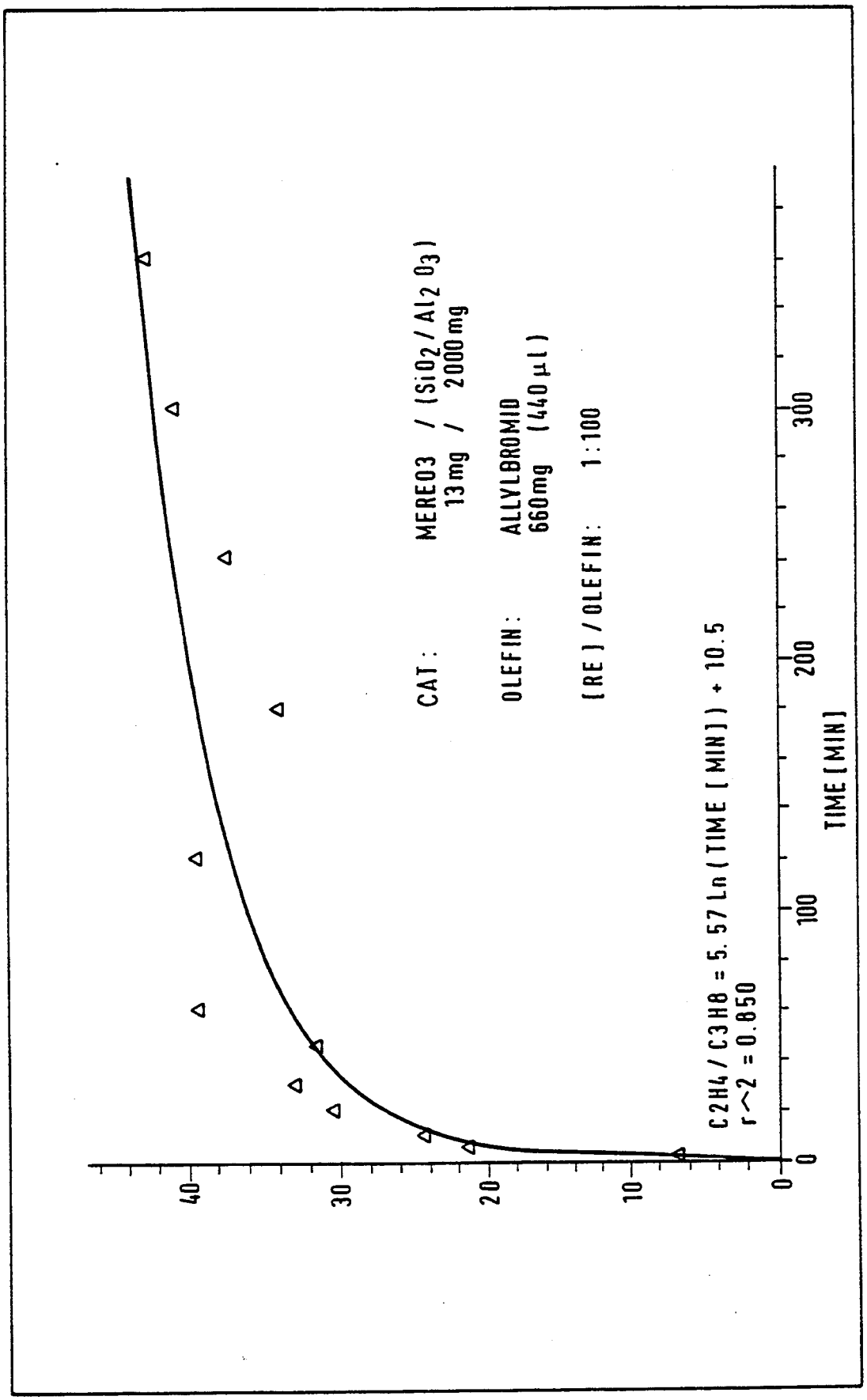
Figure 6:
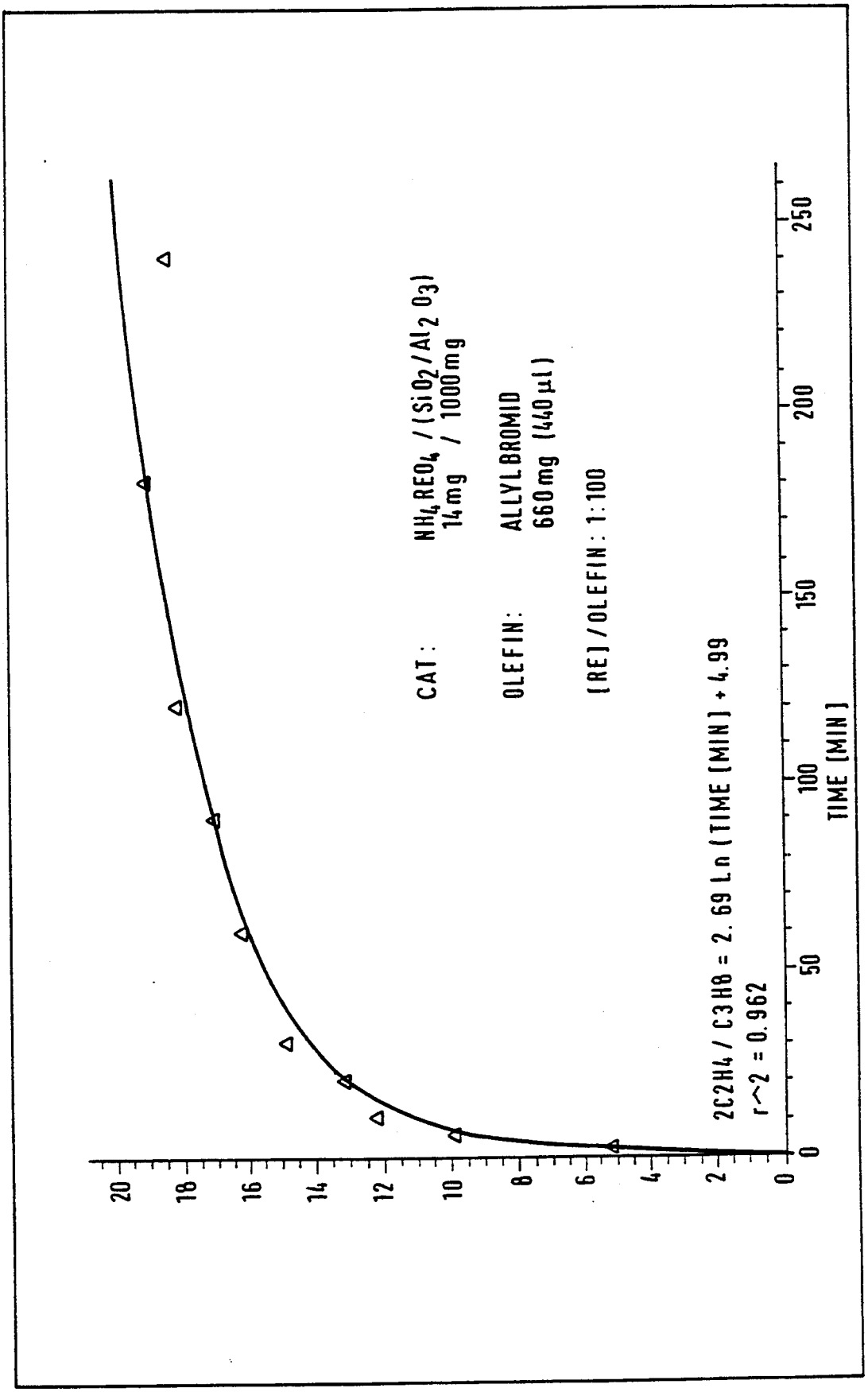
Figure 7:
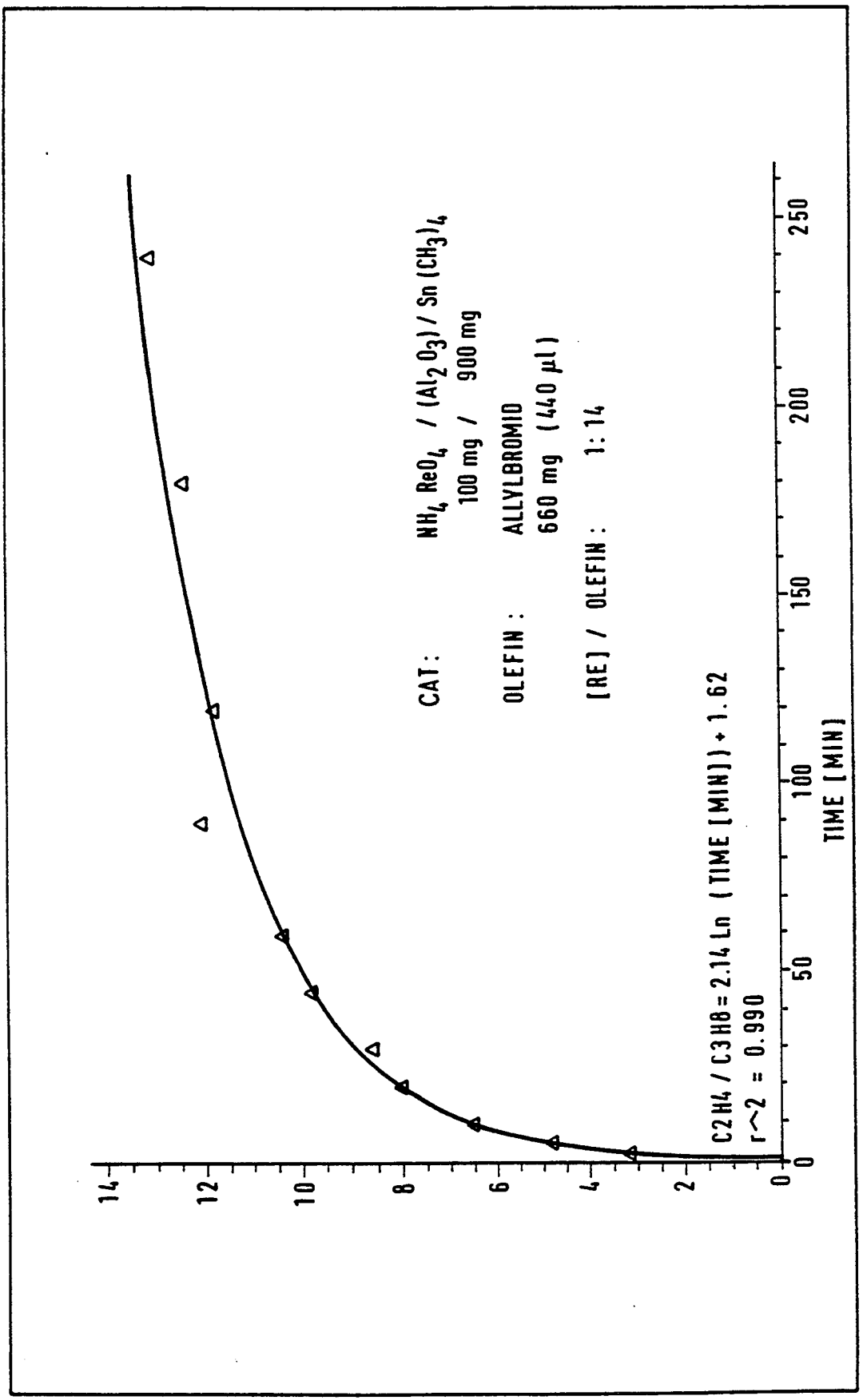

After stirring for 5 minutes 5 mmol of olefin were injected (t=0) and the ethylene content of the gas phase was determined by gas chromatography at the intervals of time evident from graphs of FIGS. 1, 2, 6 and 7. FIG. 6 shows a comparison with FIG. 1, FIG. 2 shows the effect of a greater dilution of the catalyst compared with FIG. 1 and FIG. 7 shows a comparison with the rhenium-containing catalyst system hitherto used and known from the literature, as specified by Warwel et al, loc. at. For this purpose 900 mg of neutral aluminum oxide were first impregnated with a solution of 100 mg of ammonium perrhenate $NH_4[ReO_4]$ in 10 ml of dioxane/water (9+1 parts by volume). The catalyst system was then activated at 550° C. for 2 hours in a stream of oxygen and then for 2 hours in a stream of nitrogen. The reaction kinetics tests proceeded analogously to those with methylrhenium trioxide $CH_3ReO_3$, but it was necessary for activation to inject 0.005 ml of tetramethyltin $Sn(CH_3)_4$ 5 minutes before the addition of olefin, in order to obtain any catalytic effect at all.

A direct comparison was afforded by comparison test V1, in which 14 mg of ammonium perrhenate $NH_4[ReO_4]$ were absorbed onto 1 g of $SiO_2/Al_2O_3$ and activated in a stream of $O_2$ and $N_2$ as indicated above.

Figure 3:
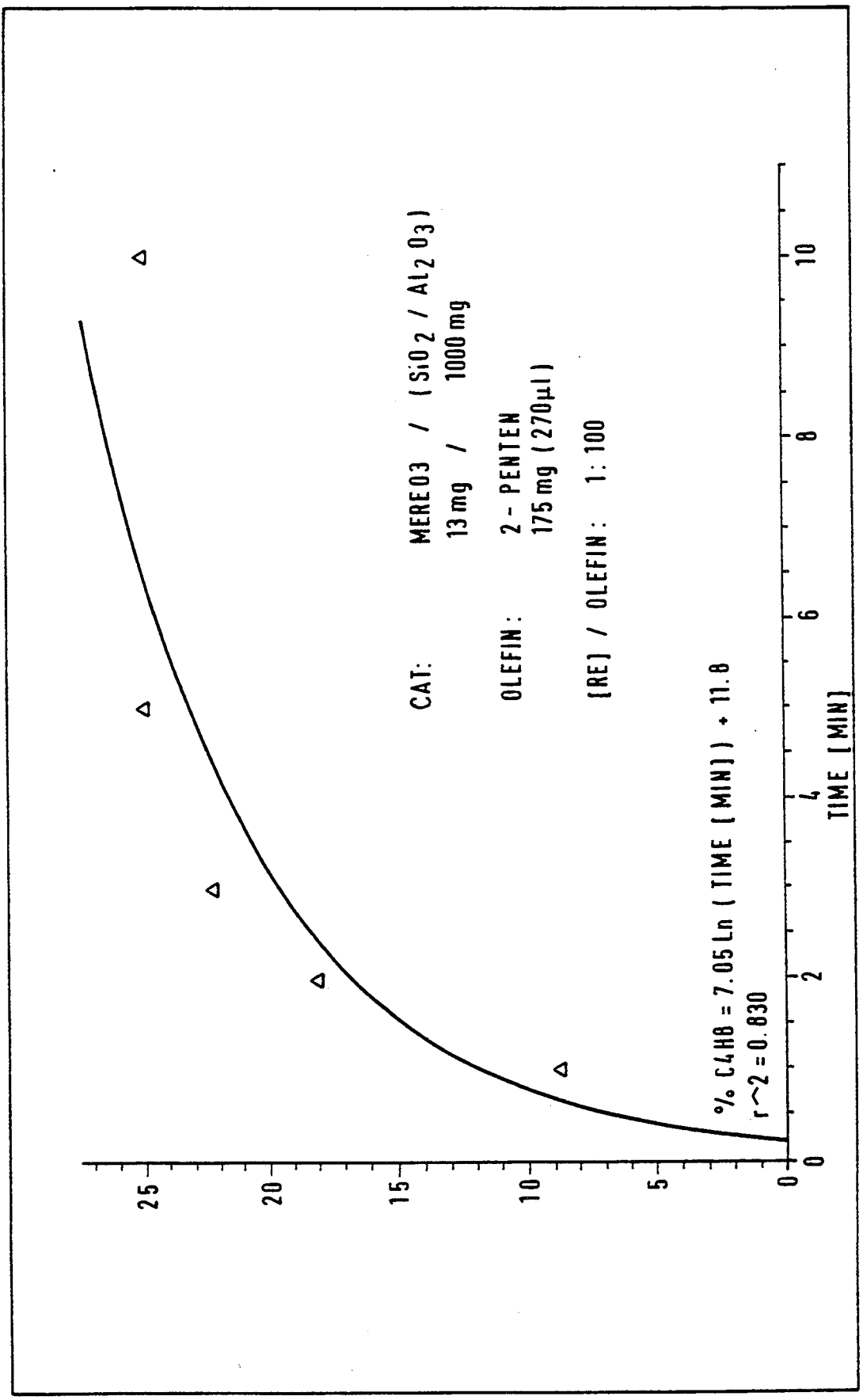
Figure 8:
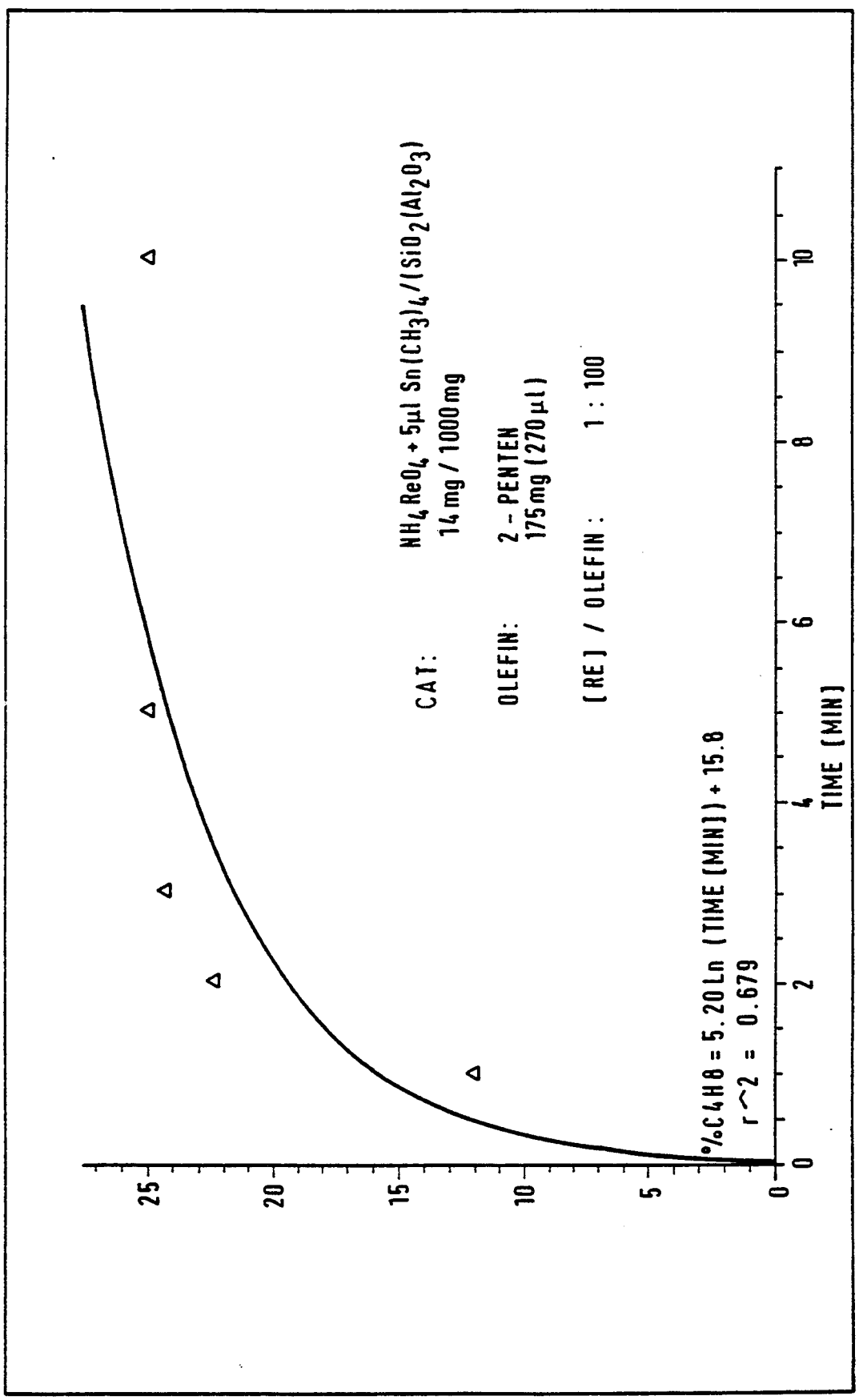

In the metathesis of olefins as such $CH_3ReO_3$ on the one hand and $NH_4[ReO_4]$ on the other hand achieved a comparable activity on $SiO_2/Al_2O_3$. The equilibrium product distribution in the metathesis of a mixture of 50 mol % of 2-pentene+25 mol % of 2-butene+25 mol of 3-hexene was set up after approx. 5 minutes in both systems, but in the case of $NH_4[ReO_4]$ only after additional activation with tetramethyltin, as can be seen from a comparison of the graphs of FIGS. 3 and 8.

Effects Arising From the Catalyst Support

As shown in particular by the systems of FIGS. 1 and 2 for the metathesis of allyl bromide, the activity of the catalyst $CH_3ReO_3$ increases greatly with dilution (relative to the amount of oxide supporting material): For a reaction time of 300 minutes, 13 mg of $CH_3ReO_3+1000$ mg of $SiO_2/Al_2O_3$ give a value of 30 for Q, while 13 mg of $CH_3ReO_5+2000$ mg of $SiO_2/Al_2O_3$ give a value of 40 for Q.

EXAMPLES 6-9

Metathesis Using $(CH_3)_6Re_2O_3$

Figure 4:
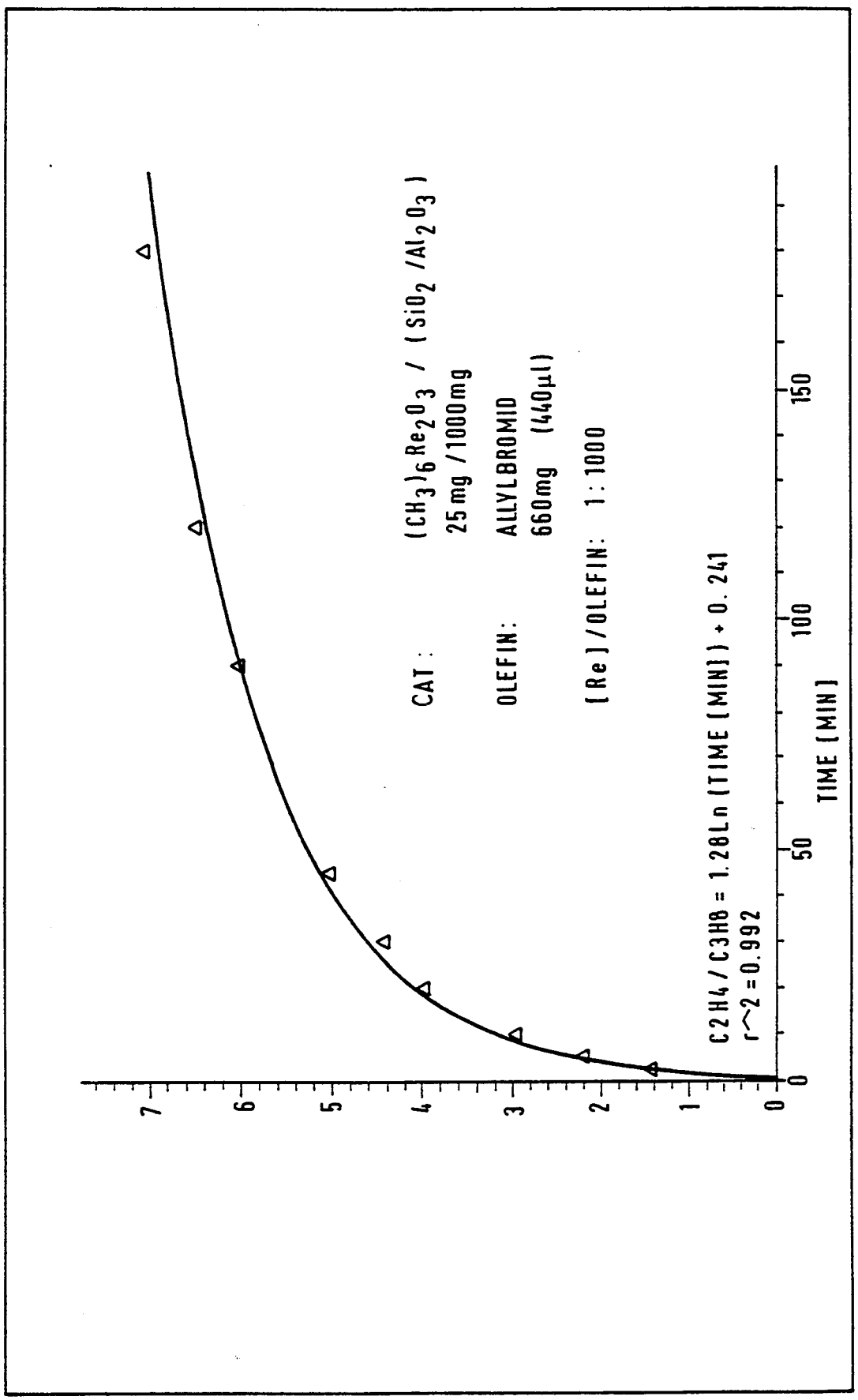

6) In a 30 ml reaction vessel closed with a septum, a solution of 25.5 mg (0.052 mmol) of hexamethyltrioxodirhenium $(CH_3)_6Re_2O_3$ in 0.5 ml of methylene dichloride was introduced with stirring into a suspension of 1000 mg of catalyst support ($SiO_2/Al_2O_3$; weight ratio 87:13, particle size below 15 μm; kept at 800° C. for 2 hours) in 10 ml of methylene dichloride (dried over calcium hydride and stored under an atmosphere of nitrogen). 0.5 ml of propane were injected as the internal standard. After stirring for 5 minutes 5 mmol of allyl bromide were injected (t=0) and the ethylene content of the gas phase was determined by gas chromatography at the intervals of time evident from the graph of FIG. 4.

7-9) In a 30 ml reaction vessel equipped with a septum, a reflux condenser and a mercury pressure relief valve, a solution of 25.5 mg (0.052 mmol) of hexamethyltrioxodirhenium $(CH_3)_6Re_2O_3$ in 0.5 ml of methylene dichloride was introduced with stirring into a suspension of 1000 mg of catalyst support [$SiO_2/Al_2O_3$ (87:13), particle size below 15 μm (preparation No. 14-7150 of Strem Chemicals, Newburyport/Mass. 01950 (USA), heated at 800° C. for 2 hours] in 10 ml of methylene dichloride (dried over calcium hydride and kept under an atmosphere of nitrogen). The contents of the flask were heated to the boil. After thermal equilibrium had been set up, 5.2 mmol of olefin were injected through the septum by means of a syringe. In order to isolate the product, the mixture was boiled under reflux for several hours (Table 2), the contact catalyst was filtered off with suction on a frit and was washed with twice 10 ml of methylene dichloride. The solvent was stripped off in an oil pump vacuum, the product was weighed and its purity was checked by means of a gas chromatograph with coupled mass spectrometer.

TABLE 2

| Example/olefin (*) | Time (hrs) | Amount (mg) | Weight (mg) | Purity (%) | Yield (%) |
|---|---|---|---|---|---|
| 7) Allyl bromide | 20 | 680 | 72 | 98 | 12 |
| 8) Ethyl undecenoate | 20 | 1410 | 840 | 57 | 34 |
| 9) Allyl trimethylsilyl ether | 15 | 705 | 550 | 48 | 41 |

(*) Metathesis products:
7) 1,4-Dibromobut-2-ene.
8) Diethyl eicos-10-ene-1,1'-dicarboxylate.
9) 1,4-Bis-(trimethylsiloxy)-but-2-ene.

EXAMPLE 10

Metathesis Using $(CH_3)_4Re_2O_4$

Figure 5:
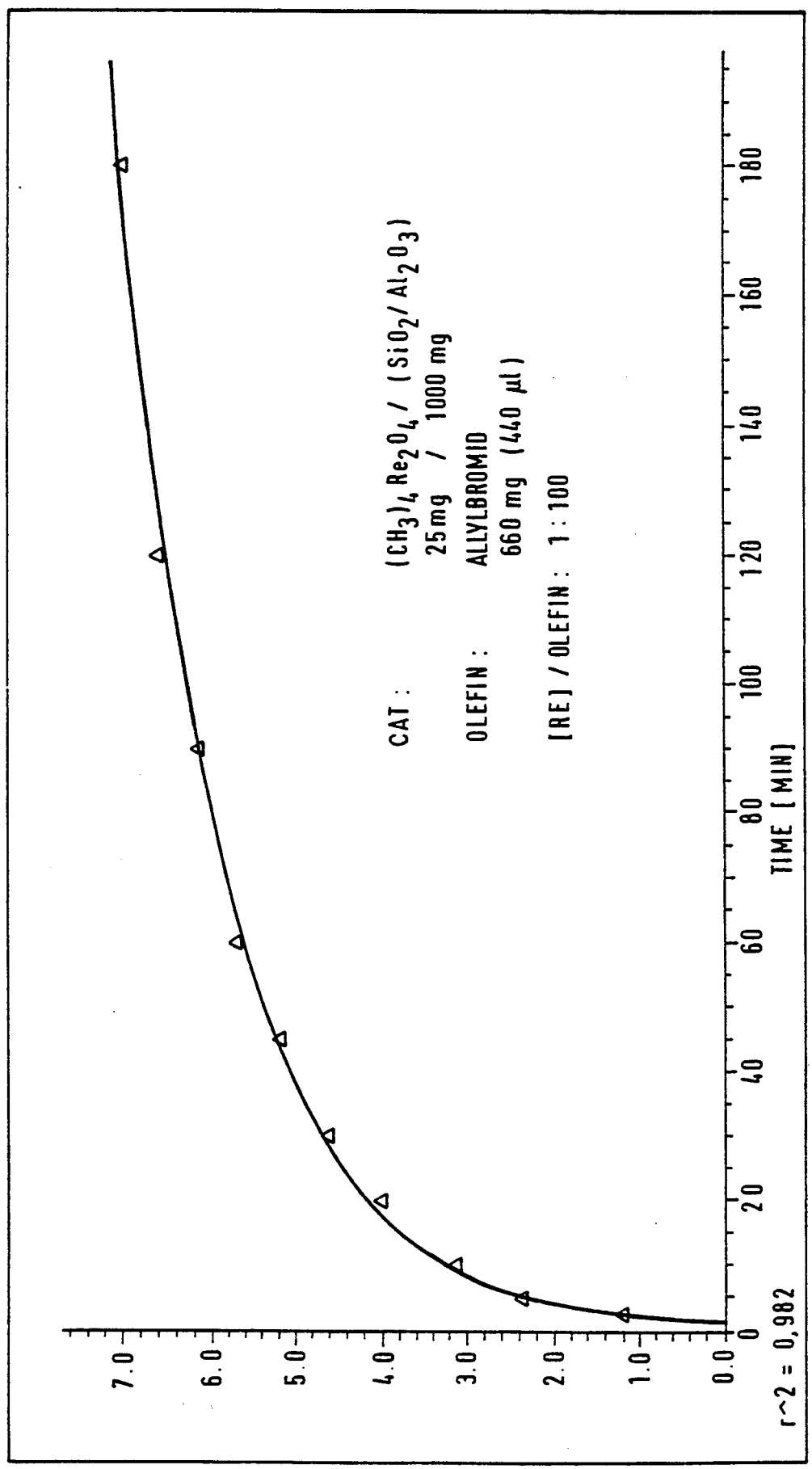

In a 30 ml reaction vessel closed by means of a septum, a solution of 25.8 mg (0.052 mmol) of tetramethyltetraoxodirhenium $(CH_3)_4Re_2O_4$ in 0.5 ml of methylene dichloride was introduced with stirring into a suspension of 1000 mg of catalyst support ($SiO_2/Al_2O_3$; weight ratio 87:13, particle size below 15 μm; kept at 800° C. for 2 hours) in 10 ml of methylene dichloride (dried over calcium hydride and kept under an atmosphere of nitrogen). 0.5 ml of propane were injected as the internal standard. After stirring for 5 minutes 5 mmol of allyl bromide were injected (t=0) and the ethylene content of the gas phase was determined by gas chromatography at the intervals of time evident from the graph of FIG. 5.

EXAMPLES 11–15

Compounds of the Formula $R^1_a Re_b O_c$

11. Trimethyl(oxo)rhenium, $(CH_3)_3ReO$ a) 2.62 g (10 mmol) of triphenylphosphine $P(C_6H_5)_3$ and 10.85 g (0.1 mol) of trimethylchlorosilane $(CH_3)_3SiCl$ were added rapidly, successively and at room temperature and with vigorous magnetic stirring to a solution of 4.14 g (10 mmol) of the compound $[(CH_3)_3SnO]ReO_3$ in 100 ml of anhydrous tetrahydrofuran. After 3 hours stirring at room temperature a green deposit had formed, consisting of the compound $ReOCl_3[OP(C_6H_5)](OC_4H_8)$ ($OC_4H_8$=tetrahydrofuran). Filtering off this precipitate from the supernatant solution, washing it with tetrahydrofuran and drying it in an oil pump vacuum gave 6.19 g (94% of theory) of this compound in a pure form.

b) 3.29 g (5 mmol) of the compound prepared under a) were suspended in 20 ml of tetrahydrofuran. A 0.2-molar solution of lithiummethyl $LiCH_3$ (altogether 16 mmol) were added dropwise at 0° C. to this suspension, and the resulting reaction mixture was stirred for a further 3 hours at room temperature. The volatile constituents were then removed in an oil pump vacuum. The dark brown residue, in most cases somewhat oily, was extracted with approx. 10 ml of toluene. The extract was evaporated to dryness in an oil pump vacuum. The residue was chromatographed at −60° C. on a column (40 cm long and 2 cm in diameter) of silanized, calcined silica gel (by Merck), the yellow zone of the compound $(CH_3)_3ReO$ being developed with toluene. The eluate was concentrated under an oil pump vacuum. The residue was then dissolved in 20 ml of n-pentane, and the solution was left to crystallize at −80° to −400° C. This gave 198 mg (16% of theory) of yellow needles of $(CH_3)_3ReO$.

Characterization: Soluble in the customary anhydrous organic solvents, in particular methylene chloride, tetrahydrofuran and toluene. The substance is solid and, in solution, admittedly only stable undecomposed for some time when stored within the temperature range from −80° to −40° C. IR (cm−, KBr): 978 sst [v(Re=O)]. $^1$H-NMR (270 MHz; 28° C., $CD_2Cl_2$): δ $CH_3$=5.41 (singlet). FD-mass spectrum: Molecule ion m/z=248 ($^{187}$Re), with correct pattern of isotopes $^{185}$Re/$^{187}$Re.

12. Tris(neopentyl)oxorhenium, $Re[(CH_2C(CH_3)_3]_3O$

This compound was synthesized analogously to the instructions for Example 11, employing lithiumneopentyl $Li[CH_2C(CH_3)_3]$ instead of lithiummethyl. The product was worked up analogously. Yield 249 mg (12% of theory).

Characterization: Yellow crystals; stable without decomposition over a prolonged period (approx. 8 days) only at temperatures below −20° C. IR (cm−1, KBr): 975 cm−1 sst [v(Re=O)]. $^1$H-NMR (400 MHz, 28° C., $CDCl_3$): δ $CH_3$=1.12 (singlet, 9H), δ $CH_2$=2.21 [somewhat broadened singlet, 2H]. FD mass spectrum: Molecule ion m/z=416 ($^{187}$Re), with correct pattern of isotopes $^{185}$Re/$^{187}$Re.

13. 2,2,2-Triftuoroethyltrioxorhenium, $(CF_3CH_2)ReO_3$ 20 mmol of a 0.5-molar solution of bis-(2,2,2-trifluoroethyl)zinc $Zn(CH_2CF_3)_2$ in tetrahydrofuran was added dropwise at room temperature and in the course of 10 minutes to a solution of 4.84 g (10 mmol) of dirhenium heptoxide $Re_2O_7$ (by Degussa, 76.9% of Re) in 100 ml of an anhydrous solvent such as tetrahydrofuran, and the mixture was then stirred for a further 80 minutes at room temperature. The volatile constituents were then stripped off in an oil pump vacuum into a cold trap, cooled with liquid nitrogen. The residue was sublimed in a high vacuum at 40°–85° C. onto a water-cooled sublimation finger. This gave 2.41 g (38% of theory) of slightly yellowish needle-shaped crystals of the compound $(CF_3CH_2)ReO_3$. The synthesis is also possible using unsublimed $Re_2O_7$, but the yields are then lower (in the range of 10–18%).

The substance has the following characteristics: Soluble in most anhydrous organic solvents, especially in tetrahydrofuran, methylene chloride and toluene, forming virtually colorless, light-sensitive solutions. IR (cm−1, KBR: 1048 st, 960 sst [v(Re=O]. $^1$O-NMR ($CDCl_3$, 28° C.: δ ($CH_2$)=2.30 [quartet]. $^{17}$O-NMR ($CDCl_3$, 28° C.): δ (O)=590 ppm. EI-MS: m/z=318 (molecule ion with correct pattern of isotopes $^{185}$Re/$^{187}$Re). The substance can be kept without decomposition at ice temperature (0° C.), if care is taken to exclude light. Elementary analysis: Calculated for $C_2H_2F_3O_3Re$ (317.21): C 7.57, H 0.63, F 17.97, Re 58.70; found: C 7.60, H 0.70, F 18.00, Re 58.59.

The same compound was obtained in a yield of 40–84% when dirhenium heptoxide $Re_2O_7$ was reacted with an equimolar amount of tetrakis-(2,2,2-trifluoroethyl)-tin $Sn(CH_2CF_3)_4$ under the conditions mentioned in the preceding instructions, the only difference being that the components were reacted with one another not at room temperature, but in boiling tetrahydrofuran for 1 to 2 hours. The product was worked up analogously.

The Use of $(CH_3CH_2)ReO_5$

When this compound is used as a catalyst for olefin metathesis, the procedure is just the same as that described in Examples 1 to 5 for methylrhenium trioxide $CH_3ReO_3$.

14. (2,3,4,5,6-pentafluorophenylmethyl)-trioxorhenium, $C_6F_5CH_2ReO_3$

The corresponding Grignard compound $C_6F_5CH_2MgI$ was first prepared from a solution of 6.16 g (20 mmol) of (2,3,4,5,6-pentafluorophenyl)-methyl iodide $C_6F_5CH_2I$ by known process by reacting the latter with magnesium turnings in diethyl ether as solvent. 12.3 g (9 mmol) of anhydrous zinc chloride were then added to the resulting solution. The resulting reaction mixture was then boilded under reflux for 5 hours. The compound bis-(2,3,4,5,6-pentafluorophenylmethyl)-zinc $Zn(CH_2C_6F_5)_2$ thus obtainable could be obtained by filtration from the solution and by recrystallization at low temperatures (−80° to −40° C.).

2.14 g (5 mmol) of bis-(2,3,4,5,6-pentafluorophenyl-methyl)-zinc $Zn(CH_2C_6F_5)_2$ were added at room temperature to a solution of 4.84 g (10 mmol) of dirhenium heptoxide Re207 (by Degussa, 76.9% of Re) in 100 ml of an anhydrous solvent such as tetrahydrofuran. The resulting solution was stirred for a further 60 minutes at room temperature. The volatile constituents were then stripped off in an oil pump vacuum into a cold trap cooled with liquid air. The residue was extracted with three times 20 ml of anhydrous toluene, the extract was filtered and the filtrate was then evaporated to dryness at 0° C. under an oil pump vacuum. The residue was recrystallized at −40° to −8° C. from a solvent mixture composed of equal volumes of n-hexane and toluene. This gave 581 mg (28% of theory, relative to the zinc compound employed) of slightly yellow octahedral crystals of the catalyst ($C_6F_5CH_2$)$ReO_3$.

The substance has the following characteristics: Soluble in most of the customary anhydrous organic solvents, especially toluene, methylene chloride and tetrahydrofuran. IR (cm$^1$, KBr): 1058 st, 958 sst [v(Re=O)]. $^1$H-NMR (CDCl$_3$, 28° C.): 6(CH$_2$)=2.39 ppm [somewhat broadened singlet]. $^{17}$O-NMR (CDCl$_3$, 28° C.): δ(O)=604 ppm. EI-MS: m/z=416 (molecule ion with correct pattern of isotopes $^{185}$Re/$^{187}$Re). Elementary analysis: Calculated for C$_6$F$_5$CH$_2$ReO$_3$ (415.26): C 20.25, H 0.48, F 22.87, Re 44.84; found: C 20.20, H 0.50, F 22.60, Re 45.00.

15. Bis-[μ-oxo(oxo)dimethylrhenium(VII)], (CH$_3$)$_4$Re$_2$O$_4$ 2.40 g of dirhenium heptoxide Re$_2$O$_7$ (6.60 mmol) were dissolved in 150 ml of anhydrous tetrahydrofuran and cooled to −78° C. 0.48 ml of freshly distilled dimethyl-zinc Zn(CH$_3$)$_2$ (6.60 mmol) were added dropwise, with continuous stirring, to this solution. This must be carried out with exclusion of air and moisture, since dimethylzinc burns in the air and is decomposed by water. The solution was stirred at this temperature for 4 hours and turned a strong yellow color. The reaction temperature was not allowed to exceed −30° C. The solvent was then stripped off at −40° C. under an oil pump vacuum. The product could be sublimed in a high vacuum in thin yellow needles from the residue which remained. Yield: 1.64 g (50% of theory). Melting point 120° C. (without decomposition).

| C$_4$H$_{12}$Re$_2$O$_4$: (476.5) | Calc.: Found: | C 9.64 C 9.60 | H 2.41 H 2.48 | O 12.85 O 12.79 |
|---|---|---|---|---|

EI mass spectrum: m/e=498 (molecule ion [M+]), m/e 249 (base peak [½ M]).

Infrared spectrum: (cm$^{-1}$, KBr): 1017/1007 sst [v(Re=0)].

1H-NMR (CDCl$_3$, 28° C.); 6(CH$_3$) 2.81 ppm, $^{13}$C-NMR (CDCl$_3$, 28° C.); δ(CH$_3$) 30.36 ppm.

The compound is stable in air and readily soluble in all customary organic solvents.

EXAMPLES 16 TO 28

Ethenolysis using (CH$_3$)ReO$_3$

A solution of 13 mg (0.052 mmol) of methylrhenium trioxide CH$_3$ReO$_3$ in 0.5 ml of dichloromethane was added to a suspension of 2000 mg of a catalyst support [SiO$_2$Al$_2$O$_3$, 87:13 percent by weight, particle size below 15 μm, heated at 550° C. for 2 hours] in 50 ml of dichloromethane (dried over calcium hydride and stored under an atmosphere of nitrogen] in a 250 ml laboratory reaction vessel. The addition was effected while stirring at the temperatures indicated in each case in table 1. After stirring for 5 minutes, 2.5 mmol of olefin was injected (t=0) and ethylene pressed in to achieve a pressure is indicated in Table 3. After a reaction time of 5 hours the reaction products indicated in Table 3 where identified in the liquid phase by gas chromatography.

TABLE 3

Ethenolysis of non-functionalised and functionalized acyclic and cyclic olefins with (CH$_3$)ReO$_3$

| Example/Starting material | Reaction conditions | Products | Yield$^{a)}$ (%) |
|---|---|---|---|
| 16) Cis/trans-3-heptene | 10 bar/40° C. | 1-Butene | 39 |
| | | 1-Pentene | 39 |
| 17) β-Di-iso-butene* | 15 bar/40° C. | 3,3-Dimethyl-1-butene | 46 |
| | | Isobutene | 45 |
| 18) 1,3-Cyclohexadiene | 8 bar/28° C. | 1,5-Hexadiene | 42 |
| | | 1,3-Butadiene | 40 |
| | | 1,4,7-Octatriene | 7 |
| 19) Cyclododecene | 8 bar/30° C. | 1,13-Tetradecadiene | 98 |
| 20) Cyclooctene | 8 bar/30° C. | 1,9-Decadiene | 91 |
| 21) 1,5-Cyclooctadiene | 15 bar/35° C. | 1,5-Hexadiene | 72 |
| | | 1,5,9-Decatriene | 12 |
| 22) Cyclopentene | 10 bar/28° C. | 1,6-Heptadiene | 80 |
| 23) 1,9-Cyclohexadecadiene | 15 bar/40° C. | 1,9,17-Octadecatriene | 12 |
| | | 1,9-Decadiene | 66 |
| 24) α,α'-Diphenylstilbene | 18 bar/65° C. | 1,1-Diphenylethylene | 53 |
| 25) 2-Norbornene | 13 bar/30° C. | 1,4-Divinylcyclopentane | 67 |
| 26) Oleic acid methylester | 15 bar/30° C. | 1-Decene | 44 |
| | | 9-Decene acid methylester | 46 |
| 27) Linolic acid ethylester | 15 bar/40° C. | 1-Heptene | 33 |
| | | 1,4-Pentadiene | 31 |
| | | 9-Decene acid ethylester | 21 |
| 28) Geranylacetone** | 14 bar/−5° C. | Isobutylene | 33 |
| | | 2-Methyl-1,5-hexadiene | 28 |
| | | 4-(1-Butenyl)-methyl-ketone | 29 |

*2,4,4-Trimethyl-2-pentene
**(CH$_3$)$_2$C=CH(CH$_2$)$_2$C(CH$_3$)=CH(CH$_2$)$_2$C(=O)CH$_3$
$^{a)}$Sum of the olefins is equivalent to the conversion rate

EXAMPLES 29 TO 32

Ethenolysis with (CH$_3$)$_4$Re$_2$O$_4$

The process was carried out in the same manner as indicated when using methylrhenium trioxide CH$_3$ReO$_3$ in Examples 16 to 28 except that instead of the solution of 13 mg methylrhenium trioxide a solution of 25.4 mg (0.052 mmol) of tetramethyl tetraoxodirhenium (CH$_3$)$_4$Re$_2$O$_4$ in 0.5 ml dichloromethane was added to the suspension of 2000 mg of the catalyst support. After a reaction period of 5 hours the compounds indicated in Table 4 were identified by gas chromatography.

TABLE 4

Ethenolysis of olefins with (CH$_3$)$_4$Re$_2$O$_4$ on SiO$_2$/Al$_2$O$_3$

| Example/Starting material | Reaction conditions | Products | Yield$^{a)}$ (%) |
|---|---|---|---|
| 29) Cis/trans-3-heptene | 10 bar/40° C. | 1-Butene | 35 |
| | | 1-Pentene | 35 |
| 30) 1,3-Cyclohexadiene | 10 bar/30° C. | 1,5-Hexadiene | 34 |
| | | 1,3-Butadiene | 30 |
| | | 1,3,7-Octatriene | 10 |
| 31) Cyclopentene | 20 bar/30° C. | 1,6-Heptadiene | 75 |
| 32) Oleic acid methylester | 15 bar/30° C. | 1-Decene | 46 |
| | | 9-Decene acid methylester | 44 |

$^{a)}$Sum of the olefins is equivalent to the conversion rate

We claim:
1. A process for the metathesis of olefins which comprises reacting an olefin of the formula

YCZ=CZ—(CX$_2$)$_n$R$^2$ (II)

wherein n is an integer from 1 to 28,

X represents H or F,

Y represents H or alkyl having from 1 to 10 carbon atoms and

Z represents H or a non-aromatic hydrocarbon group having from 1 to 6 carbon atoms and $R^2$ represents H, alkyl, halogen, $COOR^3$ or $OR^4$, wherein $R^3$ and $R^4$ represent alkyl having from 1 to 15 carbon atoms or phenyl which is unsubstituted or contains from 1 to 3 substituents or wherein $R^4$ is trialkylsilyl $R^5_3Si$, wherein $R^5$ represents alkyl having from 1 to 5 carbon atoms, at a catalyst comprising an oxidic carrier charged with a rhenium compound of the general formula $R^1_aRe_bO_c$, wherein a is an integer from 1 to 6, b is an integer from 1 to 4 and c is an integer from 1 to 14 and the sum of a, b and c conforms to the 5- to 7-valency of rhenium with the proviso that c does not exceed 3.b, and wherein $R^1$ represents alkyl having from 1 to 9 carbon atoms, cycloalkyl having from 5 to 10 carbon atoms or aralkyl having from 7 to 9 carbon atoms and wherein $R^1$ is unsubstituted or at least partially fluorinated, said compounds containing not more than three compounds of more than 6 carbon atoms per rhenium atom and containing a hydrogen atom bound to the carbon atom in a α-position to the rhenium atom wherein the reaction is carried out in the absence of $AlCl_3$.

2. A process as claimed in claim 1, wherein $R^4$ is alkyl having from 1 to 6 carbon atoms.

3. A process as claimed in claim 1, having from 1 to 3 carbon atoms.

4. A process as claimed in claim 1, wherein the olefin of the formula II is a functionalized olefin which is subjected to the metathesis reaction.

5. A process as claimed in claim 1, wherein the olefin of the formula II is a cycloolefin which is subjected to the metathesis reaction.

6. A process as claimed in claim 1, wherein the carrier comprises alumina or a combination thereof with silica and has been dried by glowing.

7. A process as claimed in claim 1, wherein the catalyst contains as the active ingredient methylrhenium trioxide $CH_3ReO_3O_3$.

8. A process as claimed in claim 1, which is carried out at a temperature in the range from 0° to 60° C. in the absence of ethylene.

9. A process as claimed in claim 8, wherein the reaction is carried out at a temperature in the range of from 10° to 30° C.

10. A process as claimed in claim 1, which is carried out at ambient pressure.

11. A process as claimed in claim 1, wherein an olefin II in which Y and Z do not simultaneously mean hydrogen is subjected to an ethenolytic metathesis by reaction with ethylene.

12. A process as claimed in claim 11, wherein the reaction is carried out at a pressure in the range of from 3 to 30 bar ethylene.

13. A process as claimed in claim 12, wherein the reaction is carried out at a pressure in the range of from 5 to 20 bar ethylene.

14. A process as claimed in claim 11, which is carried out at a temperature in the range of from −25° to +70° C.

15. A process as claimed in claim 14, which is carried out at a temperature in the range of from +20° to +65° C.

16. A process as claimed in claim 1, wherein the carrier comprises alumina, silica, an oxide of titanium, zirconium, niobium, tantalum, chromium or a combination thereof.

17. A process for the metathesis or olefins which comprises reacting an olefin of the formula $$YCZ=CZ-(CX_2)_nR^2 \text{(II)}$$

wherein n is an integer from 1 to 28,

X represents H or F,

Y represents H or alkyl having from 1 to 10 carbon atoms and

Z represents H or a non-aromatic hydrocarbon group having from 1 to 6 carbon atoms and $R^2$ represents H, alkyl, halogen, $COOR^3$ or $OR^4$, wherein $R^3$ and $R^4$ represent alkyl having from 1 to 15 carbon atoms or phenyl which is unsubstituted or contains from 1 to 3 substituents or wherein $R^4$ is trialkylsilyl $R^5_3Si$, wherein $R^5$ represents alkyl having from 1 to 5 carbon atoms, at a catalyst comprising an oxidic carrier charged with a rhenium compound of the general formula $R^1_aRe_bO_c$, wherein a is an integer from 1 to 6, b is an integer from 1 to 4 and c is an integer from 1 to 14 and the sum of a, b and c conforms to the 5- to 7-valency of rhenium with the proviso that c does not exceed 3.b, and wherein $R^1$ represents alkyl having from 1 to 9 carbon atoms, cycloalkyl having from 5 to 10 carbon atoms or aralkyl having from 7 to 9 carbon atoms and wherein $R^1$ is unsubstituted or at least partially fluorinated, said compounds containing not more than three compounds of more than 6 carbon atoms per rhenium atom and containing a hydrogen atom bound to the carbon atom in a α-position to the rhenium atom, wherein the reaction is carried out in the absence of an activating compound.

* * * * *